(12) United States Patent
Sankaran et al.

(10) Patent No.: US 10,314,654 B2
(45) Date of Patent: Jun. 11, 2019

(54) SYSTEMS AND METHODS FOR SIMULATION OF HEMODIALYSIS ACCESS AND OPTIMIZATION

(71) Applicant: HeartFlow, Inc., Redwood City, CA (US)

(72) Inventors: Sethuraman Sankaran, Palo Alto, CA (US); Leo J. Grady, Millbrae, CA (US); Charles A. Taylor, Menlo Park, CA (US); Christopher K. Zarins, Menlo Park, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

(21) Appl. No.: 15/054,622

(22) Filed: Feb. 26, 2016

(65) Prior Publication Data

US 2016/0175053 A1 Jun. 23, 2016

Related U.S. Application Data

(63) Continuation of application No. 14/595,503, filed on Jan. 13, 2015, now Pat. No. 9,336,354.

(60) Provisional application No. 62/074,698, filed on Nov. 4, 2014.

(51) Int. Cl.
| | | |
|---|---|---|
| *A61B 34/10* | (2016.01) | |
| *G06F 17/50* | (2006.01) | |
| *A61M 1/00* | (2006.01) | |
| *A61M 1/36* | (2006.01) | |
| *G16H 50/50* | (2018.01) | |
| *G06F 19/00* | (2018.01) | |
| *G16H 50/30* | (2018.01) | |

(52) U.S. Cl.
CPC ............... *A61B 34/10* (2016.02); *A61M 1/00* (2013.01); *A61M 1/3655* (2013.01); *A61M 1/3659* (2014.02); *A61M 1/3661* (2014.02); *G06F 19/00* (2013.01); *G16H 50/50* (2018.01); *A61B 2034/104* (2016.02); *A61B 2034/105* (2016.02); *A61M 1/3653* (2013.01); *G16H 50/30* (2018.01)

(58) Field of Classification Search
None
See application file for complete search history.

(56) References Cited

U.S. PATENT DOCUMENTS

| 8,315,812 B2 | 11/2012 | Taylor |
| 2014/0073976 A1 | 3/2014 | Fonte et al. |
| 2014/0073977 A1 | 3/2014 | Grady et al. |
| 2014/0249790 A1 | 9/2014 | Spilker et al. |

OTHER PUBLICATIONS

Caroli et al. (Kidney International (2013) vol. 84:1237-1245; published May 29, 2013).
Sankaran et al. (Annals of Biomedical Engineering (2012) vol. 40:2228-2242).
Antiga et al. (Med. Biol. Eng. Comput. (2008) vol. 46:1097-1112).
Bode et al. (PLoS One (2012) vol. 7:e34491, 1-8).
Huberts (Personalized Computational Modeling of Vascular Access Creation; Thesis for Technische Universiteit Eindohoven (2012); printed by Proefschrifmaken.nl; pp. 1-226).
Taylor et al. (Computer Methods in Applied Mechanics and Engineering (1998) vol. 158:155-196).
Taylor et al. (Annu. Rev. Biomed. Eng. (2009) vol. 11:109-134).
Zangan and Falk (Semin Intervent Radiol (2009) vol. 26:144-150).
M. A. G. Merkx et al.: "Assisting Vascular access surgery planning for hemodialysis by using MR, image segmentation techniques, and computer simulation", Medical and Biological Engineering and Computing., vol. 51, No. 8, Aug. 1, 2013 (Aug. 1, 2013), pp. 879-889.
International Search Report and Written Opinion for corresponding Application No. PCT/US2015/057731, dated Feb. 15, 2016, (14 pages).

*Primary Examiner* — Lori A. Clow
(74) *Attorney, Agent, or Firm* — Bookoff McAndrews, PLLC

(57) ABSTRACT

Systems and methods are disclosed for simulating or optimizing hemodialysis access. One method includes receiving a patient-specific anatomic model of a patient's vasculature; computing a pre-treatment hemodynamic characteristic of a pre-treatment geometry of a portion of the anatomic model; simulating a post-treatment geometry of a vascular access in the portion of the anatomic model; computing a post-treatment hemodynamic characteristic of the post-treatment geometry of the portion of the anatomic model having the vascular access; and generating a representation of the pre-treatment hemodynamic characteristic or the post-treatment hemodynamic characteristic.

20 Claims, 5 Drawing Sheets

SYSTEMS AND METHODS FOR SIMULATION OF HEMODIALYSIS ACCESS AND OPTIMIZATION

RELATED APPLICATION(S)

This application is a continuation of U.S. application Ser. No. 14/595,503, filed Jan. 13, 2015, which claims priority to U.S. Provisional Application No. 62/074,698 filed Nov. 4, 2014, all of which are incorporated herein by reference in their entireties.

FIELD OF THE DISCLOSURE

Various embodiments of the present disclosure relate generally to disease assessment, treatment planning, and related methods. More specifically, particular embodiments of the present disclosure relate to systems and methods for simulating and optimizing hemodialysis access.

BACKGROUND

Hemodialysis is a process in which an external machine is used to filter blood to remove excess salt and harmful wastes. For example, blood may be sent to a hemodialysis machine and back to the patient's circulation. The blood may enter and exit a body via a vascular access. For instance, a vascular access for the blood may be created by introducing cannulas into a patient's vein. Blood may then be sent to a hemodialysis machine and back to the patient's circulation via the cannulas. To enable ease of cannulation and ensure availability of many candidate access sites, a larger vein may be used. This may be possible by shunting arterial blood flow through veins. Two kinds of vascular access procedures include—arteriovenous fistula (AVF) (in which an artery and a vein may be directly connected) and arteriovenous graft (AVG) (in which a synthetic graft may be attached between an artery and a vein). Demand for cardiac output may change from before and after treatment (e.g., pre- and post-shunting of blood flow). For example, the arteriovenous connection may increase blood pressure and blood flow in the veins. The veins may slowly adapt to this shunting by enlarging in diameter and increasing in thickness. This adaptation process might take anywhere from one month to a year. Once adapted, many different candidate sites may be available for repeated cannulation and hemodialysis.

However, the change in cardiac workload for the heart post-treatment may create a health risk. For instance, shunting the blood flow from an artery to a vein may reduce overall system resistance, thus changing hemodynamics in a way that increases cardiac output. This increased demand for cardiac output may result in a larger workload for the heart, and may be linked to an increased risk of congestive heart failure. Further, treatment may change vessel geometry, thus altering regions in vessels that may be prone to thrombosis. An optimal AVG may minimize regions of disturbed hemodynamics and, consequently, minimize regions prone to thrombosis.

Thus, a desire exists to ensure that there is enough blood flow to allow successful dialysis and maintain sufficient perfusion to extremities, and at the same time, ensure that change to hemodynamics is minimal so that cardiac demand may not increase to a point that endangers a patient. Furthermore, a desire exists to improve treatment planning by optimizing vascular access graft locations and/or vascular access graft types. The present disclosure is directed to improving treatment planning by predicting changes in hemodynamics that may result from vascular access procedures.

The foregoing general description and the following detailed description are exemplary and explanatory only and are not restrictive of the disclosure.

SUMMARY

According to certain aspects of the present disclosure, systems and methods are disclosed for simulating and optimizing hemodialysis access.

One method includes: receiving a patient-specific anatomic model of a patient's vasculature; computing a pre-treatment hemodynamic characteristic of a pre-treatment geometry of a portion of the anatomic model; simulating a post-treatment geometry of a vascular access in the portion of the anatomic model; computing a post-treatment hemodynamic characteristic of the post-treatment geometry of the portion of the anatomic model having the vascular access; and generating a representation of the pre-treatment hemodynamic characteristic or the post-treatment hemodynamic characteristic.

In accordance with another embodiment, a system for simulating or optimizing hemodialysis access: a data storage device storing instructions for simulating or optimizing hemodialysis access; and a processor configured for: receiving a patient-specific anatomic model of a patient's vasculature; computing a pre-treatment hemodynamic characteristic of a pre-treatment geometry of a portion of the anatomic model; simulating a post-treatment geometry of a vascular access in the portion of the anatomic model; computing a post-treatment hemodynamic characteristic of the post-treatment geometry of the portion of the anatomic model having the vascular access; and generating a representation of the pre-treatment hemodynamic characteristic or the post-treatment hemodynamic characteristic.

In accordance with another embodiment, a non-transitory computer readable medium for use on a computer system containing computer-executable programming instructions for performing a method of simulating or optimizing hemodialysis access, the method comprising: receiving a patient-specific anatomic model of a patient's vasculature; computing a pre-treatment hemodynamic characteristic of a pre-treatment geometry of a portion of the anatomic model; simulating a post-treatment geometry of a vascular access in the portion of the anatomic model; computing a post-treatment hemodynamic characteristic of the post-treatment geometry of the portion of the anatomic model having the vascular access; and generating a representation of the pre-treatment hemodynamic characteristic or the post-treatment hemodynamic characteristic.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1:
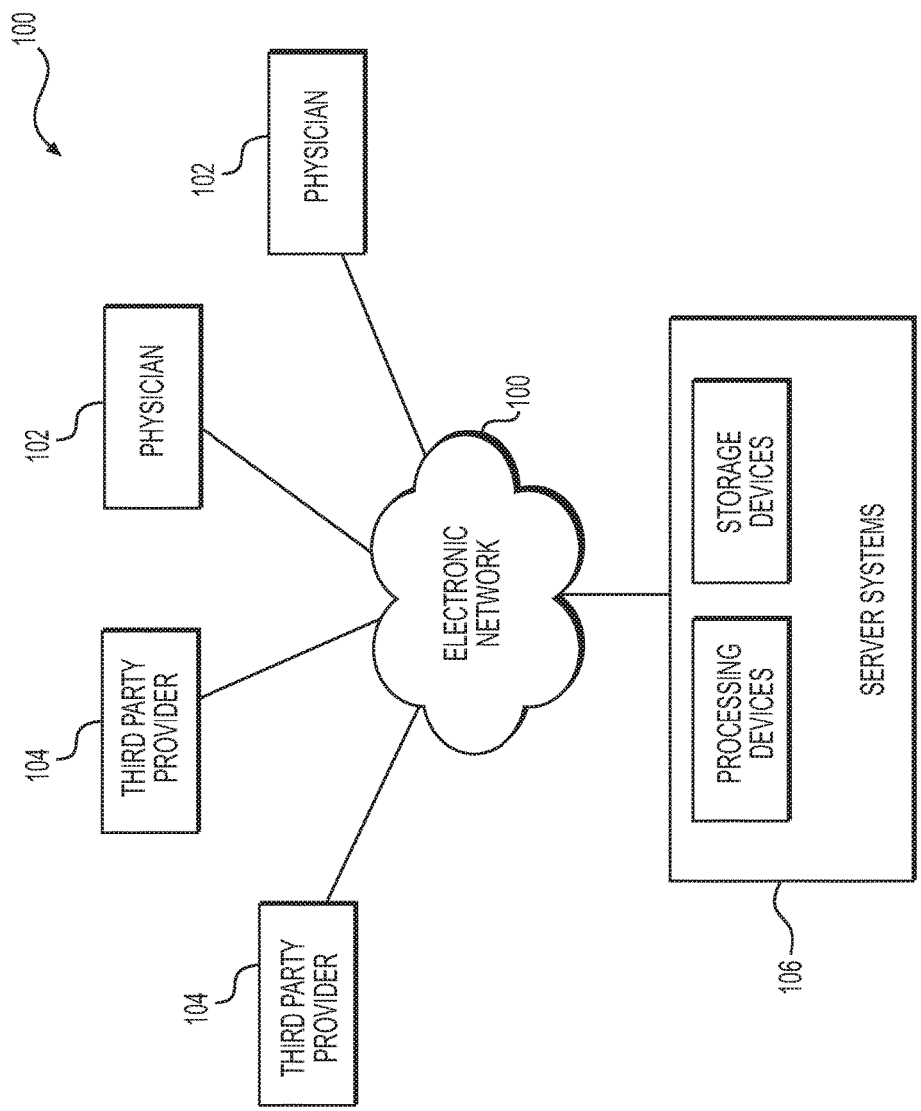
FIG. 1 is a block diagram of an exemplary system and network for simulating or optimizing hemodialysis access, according to an exemplary embodiment of the present disclosure.

Reference will now be made in detail to the exemplary embodiments of the disclosure, examples of which are illustrated in the accompanying drawings. Wherever possible, the same reference numbers will be used throughout the drawings to refer to the same or like parts.

Shunting of blood flow from an artery to a vein via AVGs or AVFs may reduce overall systemic resistance, thus causing increased cardiac output. This increased demand for cardiac output may result in a larger workload for the heart, which may be linked to an increased risk of congestive heart failure. Thus, a goal of vascular access may include increasing blood flow to the veins, while maintaining sufficient perfusion to extremities and ensuring that cardiac demand may not increase to a dangerous level. Further, an optimal AVG may minimize regions of disturbed hemodynamics so that regions prone to thrombosis may be minimized as well.

The present disclosure includes systems and methods for simulating and optimizing hemodialysis access in order to better provide vascular access that improves blood flow but does not endanger the patient. For example, the simulations and optimizations include evaluating or comparing various location(s) for the vascular access, as well as graft or fistula geometries. Each "treatment" may include vascular access at one location, multiple locations, a single graft or fistula, multiple grafts or fistulas, or a combination thereof. One embodiment may include evaluating various treatments, e.g., by simulating and comparing pre- or post-treatment blood flow for different treatments.

One embodiment may further include performing optimization for the hemodialysis access. For example, the optimization may include defining a cost function for determining an optimal hemodialysis characteristic (e.g., blood flow). The cost function may incorporate pre- and post-treatment calculations from the simulations of blood flow for different treatments. In one case, selecting or finding an optimal hemodialysis access treatment may include performing optimization over all possible vascular grafts (e.g., including graft types and/or graft locations in the patient vasculature) to minimize the cost function. In another case, the optimization may be performed for a subset of available vascular access grafts to minimize a cost function.

For example, the increase in cardiac demand due to an AVG or an AVF may be modeled by performing a pre-dialysis blood-flow simulation with the original geometry, e.g., by solving 3D Navier-Stokes equations, reduced order models, or using machine learning methods. Resistance boundary condition(s) relating blood pressure to flow rate may be provided at the model boundaries. At the aortic inlet surface, cardiac flow and pressure may be coupled to the systemic circulation using a ventricular elastance function. The ventricular elastance function may reflect the relationship between cardiac flow, pressure, and systemic circulation since pressure may be based on ventricular volume which, in turn, may be related to a flow-rate using an elastance function.

Hemodynamics post-treatment may be computed by solving the same equations using a modified geometry reflecting the procedure based on geometric variables that determine the AVG or the AVF. The resulting aortic pressure and flow rate, as well as the area enclosed in the left ventricle PV loop, may be used to estimate the changes in cardiac workload, post-treatment. The post-treatment cardiac demand and other hemodynamic quantities of interest may be reported to a user (e.g., a physician).

Hemodynamic quantities of interest may include blood flow, e.g., volume of blood or velocity of blood through a patient's vasculature or portion of a patient's vasculature. Other hemodynamic characteristics that may be quantities of interest may include shear stress and/or particle residence time through an AVG. Shear stress and particle residence time through a particular AVG may be observed to provide sufficient blood flow to allow successful dialysis, while reducing the risk of thrombosis in the AVG over time when it is not being used for dialysis. Yet another example of hemodynamic characteristics may include distal perfusion pressure and flow in arteries past a fistula. For example, evaluating distal perfusion and flow in vessel locations past an AVF may help to identify whether a graft may "steal" blood from the extremity causing ischemia/symptoms or gangrene in fingers.

Such methods may help in treatment planning and predicting changes in hemodynamics that result from vascular access procedures.

Referring now to the figures, FIG. 1 depicts a block diagram of an exemplary system 100 and network for simulating or optimizing hemodialysis access, according to an exemplary embodiment. Specifically, FIG. 1 depicts a plurality of physicians 102 and third party providers 104, any of whom may be connected to an electronic network 101, such as the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific information, such as age, medical history, blood pressure, blood viscosity, patient activity or exercise level, etc. Physicians 102 and/or third party providers 104 may transmit the anatomical images and/or patient-specific information to server systems 106 over the electronic network 101. Server systems 106 may include storage devices for storing images and data received from physicians 102 and/or third party providers 104. Server systems 106 may also include processing devices for processing images and data stored in the storage devices. For the present disclosure, "patient" may refer to any individual of interest.

Figure 2A:
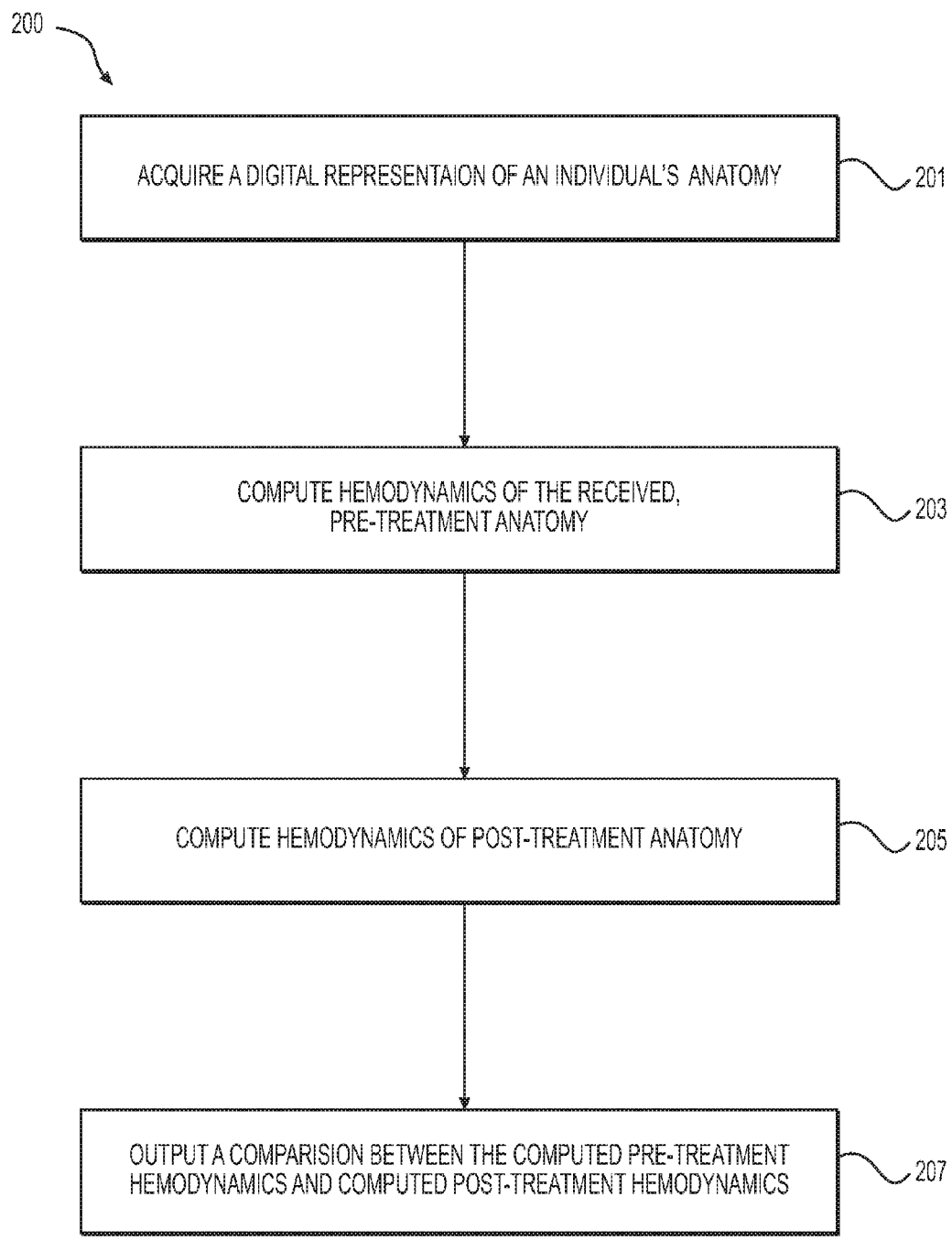
FIG. 2A is a block diagram of an exemplary method of simulating hemodialysis access, according to an exemplary embodiment of the present disclosure.
Figure 2B:
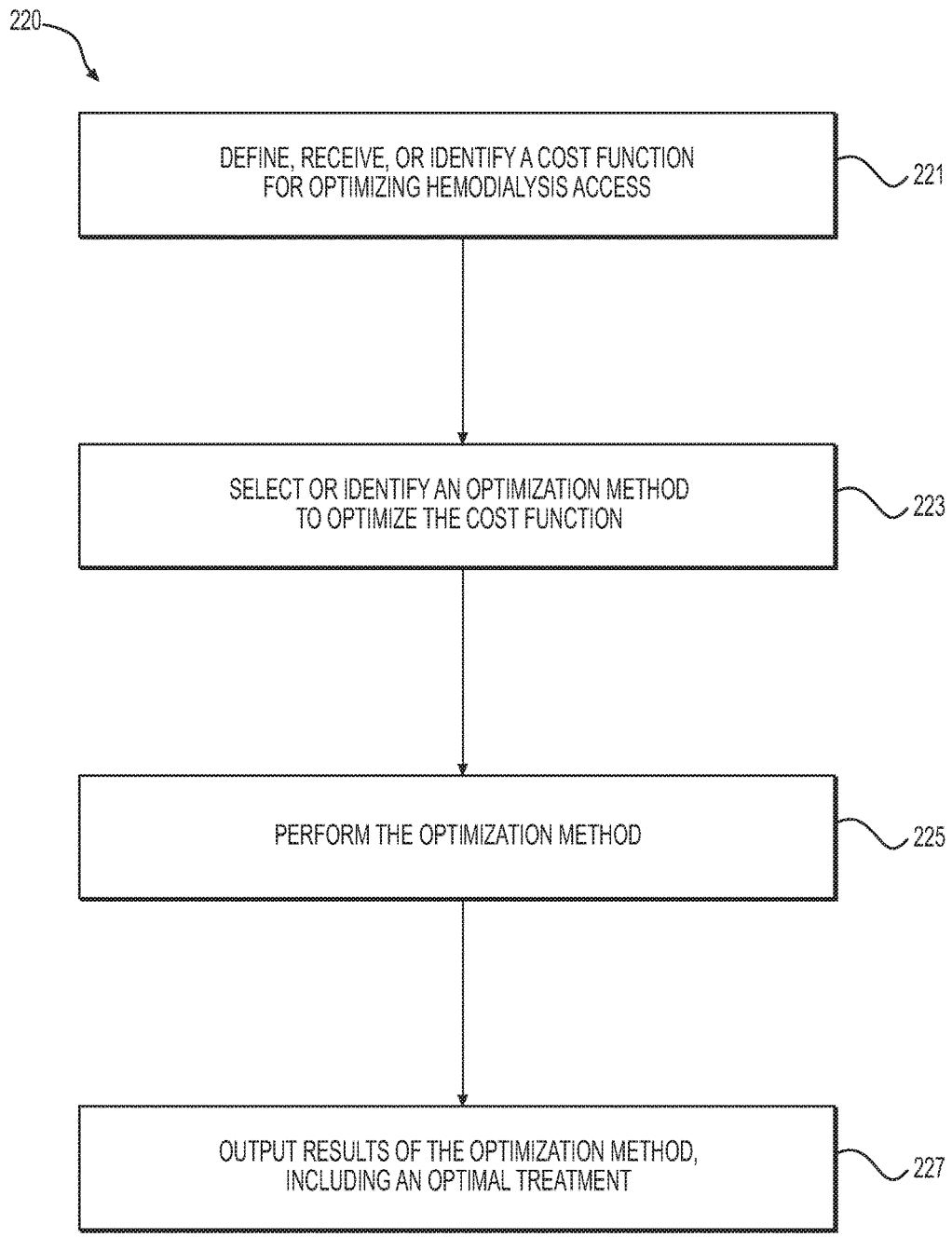
FIG. 2B is a block diagram of an exemplary method of optimizing hemodialysis access, according to an exemplary embodiment of the present disclosure.
Figure 3A:
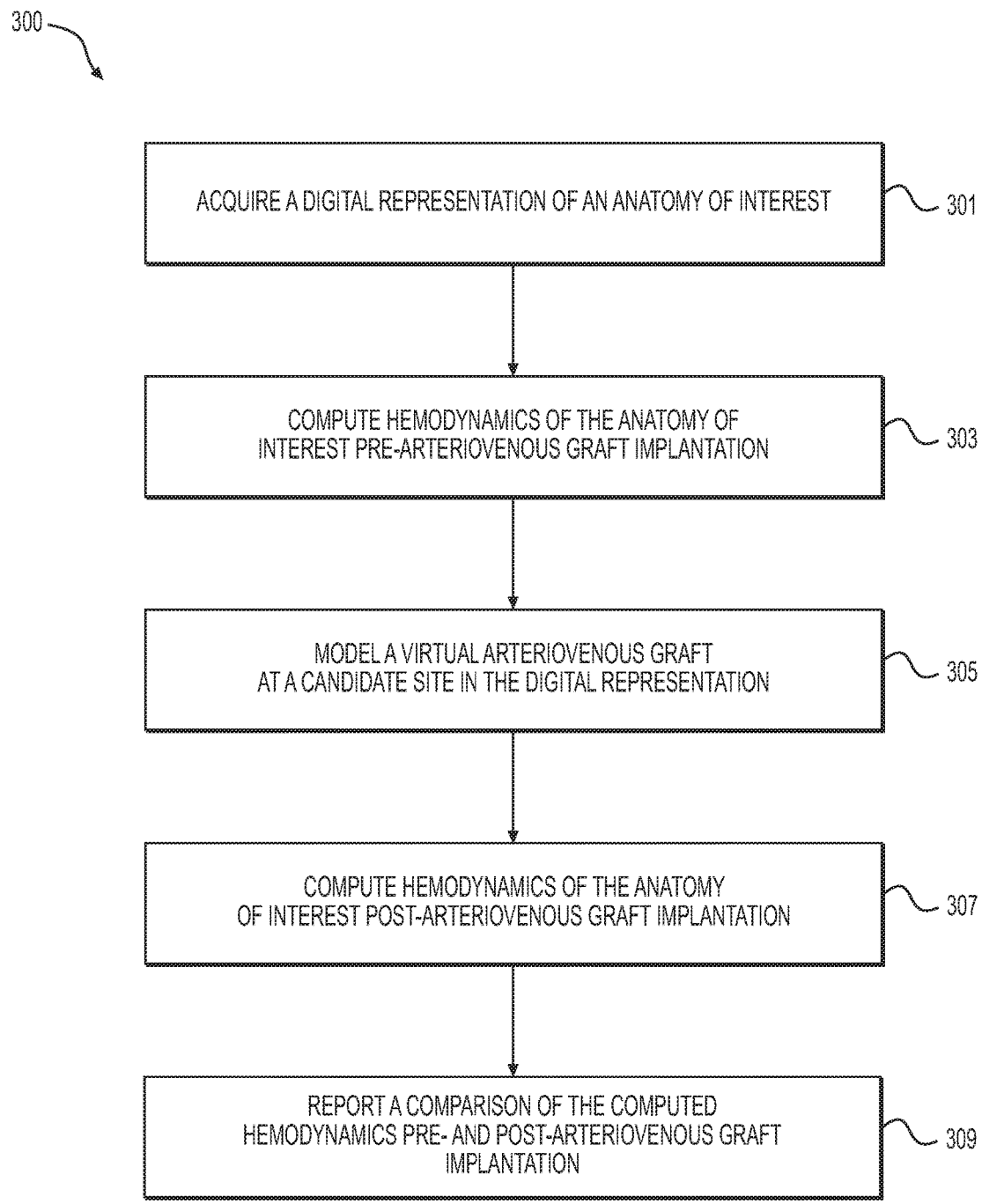
FIG. 3A is a block diagram of an exemplary method of performing predictive modeling and simulation of an AVG, a specific embodiment of simulating hemodialysis access according to an exemplary embodiment of the present disclosure.
Figure 3B:
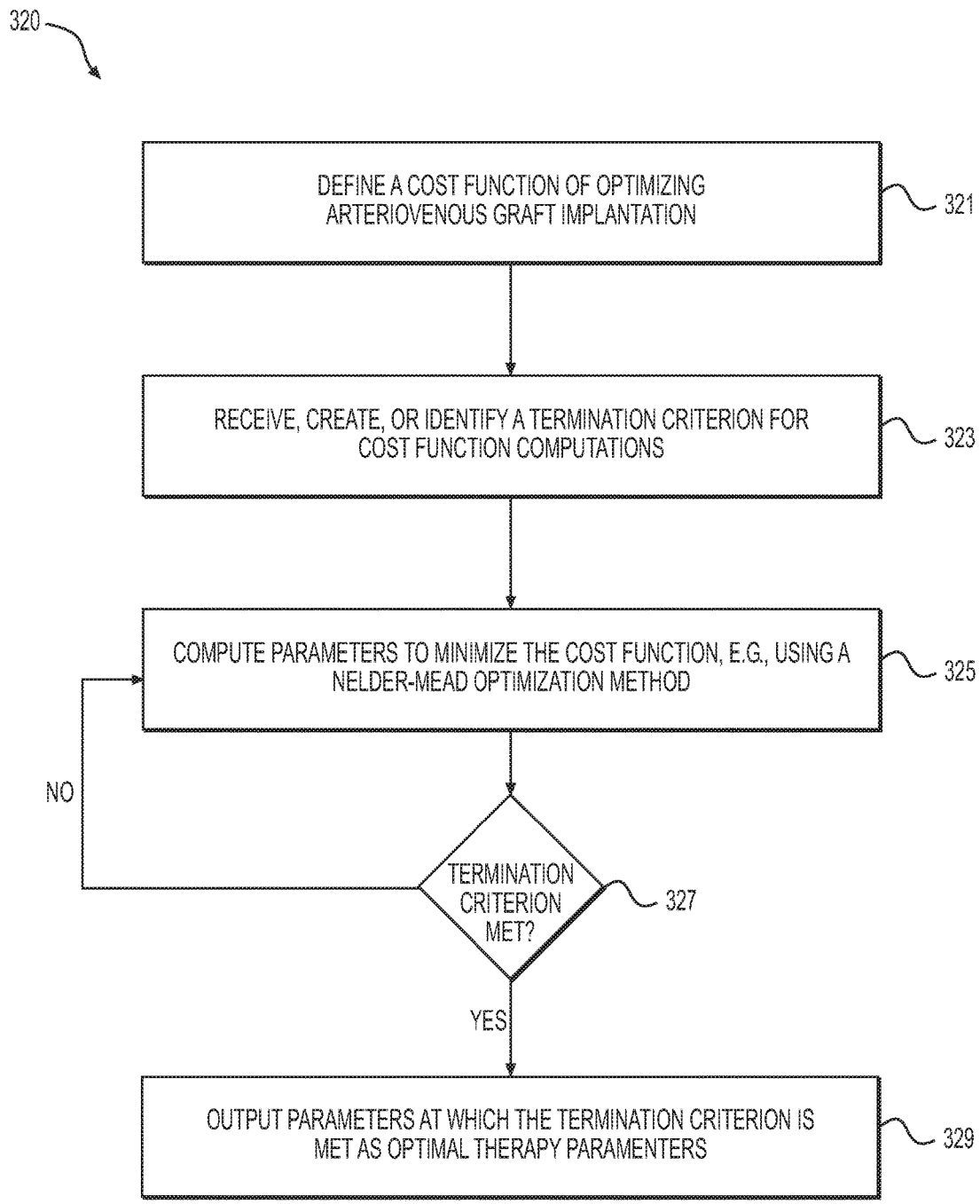
FIG. 3B is a block diagram of an exemplary method of optimizing an AVG, according to an exemplary embodiment of the present disclosure.

FIGS. 2A and 2B depict flowcharts of a general embodiment for simulating hemodialysis access and optimizing hemodialysis access, respectively. FIG. 3A depicts a flowchart of a specific embodiment for simulating hemodialysis access. FIG. 3B depicts a flowchart of a specific embodiment for optimizing hemodialysis access.

FIG. 2A is a block diagram of an exemplary method 200 of simulating hemodialysis access, according to an exemplary embodiment. The method of FIG. 2A may be performed by server systems 106, based on information, images, and data received from physicians 102 and/or third party providers 104 over electronic network 101.

In one embodiment, step 201 may include acquiring a digital representation of a system of interest (e.g., of an individual's anatomy) and reconstructing a computational model (e.g., representing the functioning of the system of interest). For example, the digital representation may include an artery and a vein that may be anastomosed or shunted, as well as all vessels branching off the arteriovenous system encompassing arteries and veins of a system of interest. In one embodiment, the vessels may be traced back to the aorta. A three dimensional model of the arteries may be reconstructed, e.g., by computing centerlines through the model and segmenting the arteries and veins across centerlines.

In one embodiment, step 201 may further include acquiring candidate parameters for anastomoses (e.g., location of an anastomosis). Step 201 may also include acquiring infeasible surgeries or any extraneous constraints that may make certain surgical configurations infeasible.

In one embodiment, step 203 may include computing hemodynamics of a pre-treatment AV system geometry. Blood flow characteristics in the reconstructed geometry may be computed by solving the Navier-Stokes equations. For example, the computation may include constructing a finite element mesh over the reconstructed geometry (e.g., from step 201) and specifying appropriate boundary conditions that relate blood pressure to flow rate at outlet surfaces. The boundary conditions may be calculated based on local tissue perfusion demand. Other boundary conditions, including capacitance of micro-vessels, may also be provided. At the aortic inlet, a time-varying elastance function of the left ventricle may be given as input. Otherwise, blood pressure or velocity may be provided as input at inlet surfaces.

Alternatively or in addition, step 203 may include using a reduced order model to solve for the hemodynamics and related quantities of interest. The reduced order model may involve combining the Poiseulle's law with non-linear stenosis pressure loss models, as well as Bernoulli's equation to account for kinetic energy of blood. Alternately or in addition, step 203 may involve solving the one dimensional wave equation.

Alternatively or in addition, step 203 may include using a machine learning approach to solve for the hemodynamics (e.g., as described in U.S. Nonprovisional application Ser. No. 13/895,893 filed May 16, 2013, the entire disclosure of which is hereby incorporated by reference in its entirety). Features of the computational model that affect hemodynamics may be calculated. In some cases, a regressor computed using a database of 3D simulations may be used to map the inputs to hemodynamic quantities of interest (e.g., as described in the application).

In one embodiment, step 205 may include simulating and computing hemodynamics for a post-treatment anatomy geometry. Post-treatment patient geometry may be created by altering the segmentation at the candidate anastomoses sites to mimic the planned treatment geometry. Any of the three broad classes of methods described in step 203 may be used to calculate hemodynamic quantities of interest post-treatment.

In one embodiment, step 207 may include outputting the results of the simulation. For example, the difference in hemodynamics pre-treatment versus post-treatment may be displayed or reported to a user (e.g., a physician). In one embodiment, step 207 may further include creating a rendering for the comparison, including graphical, pictorial, and/or interactive features.

FIG. 2B is a block diagram of an exemplary method 220 of optimizing hemodialysis access, according to an exemplary embodiment. The method of FIG. 2B may be performed by server systems 106, based on information, images, and data received from physicians 102 and/or third party providers 104 over electronic network 101.

Simulations may offer a viable alternative to calculating optimal treatment geometry, including one or more AVGs and/or AVFs at one or more locations. Optimal parameters may be computed by minimizing a cost function. In one embodiment, step 221 may include defining, receiving, or identifying a cost function for optimizing hemodialysis access. For example, a general cost function may be defined as:

$$C=\alpha_1 C_{output}(pre,post)\alpha_2 C_{flow}+\alpha_3 C_{hemo}+\alpha_4 C_{clot}+\alpha_5 C_{other}$$

$C_{output}$(pre, post) may be a function of the cardiac output of the heart, $C_{flow}$ may be a function of blood flow through the veins and flow through arteries distal to shunt location, $C_{hemo}$ may be a function of risk of clot formation near shunt location, and $C_{other}$ may be a function of any other problem-specific cost function that may depend on the hemodynamics. More specifically, the cost function may be defined as:

$$C=\alpha_1(E_{post}-E_{pre})-\alpha_2(Q_{dialyzer})+\alpha_3(H_{post}-H_{pre})+\alpha_4(T_{post}-T_{pre})+\Sigma_{i=1}^N\beta_i f_i(P,v)$$

$\alpha_1$, $\alpha_2$, $\alpha_3$, and $\alpha_4$ may include weights for different cost functions. $\alpha_2$, $\alpha_3$, and $\alpha_4$ may have different units and a user may choose to pick values based on patient-history (e.g., for a patient who has had previous coronary artery bypass graft surgery, $\alpha_2$, $\alpha_3$ and $\beta_i$ may be taken to be zero so that only the first term may be used in the optimization). E in the first term may include the difference between cardiac outputs ($E_{post}-E_{pre}$), which may be defined as:

$$E=\int PdV$$

P and V may be defined as pressure and volume of left ventricle. The second term, $Q_{dialyzer}$ may include the flow through the dialyzer intended to be maximized. H in the third term ($H_{post}-H_{pre}$), may include terms which quantify disturbed hemodynamics. For instance, H may be an area of low wall shear stresses defined as:

$$H=\int I(\tau<\tau_c)dA$$

$\tau$ may be the local WSS and $\tau_c$ may be the critical cutoff, below which surfaces may be deemed disturbed.

Furthermore, thrombosis of a graft may contribute to AVG failure. In one embodiment, the cost function may include a term (e.g., "T") that indicates a propensity for thrombosis, e.g., by modeling blood rheology or clotting. Various coagulation models T based on hemodynamics and blood viscosity may be used to account for one or more characteristics of blood that may promote or inhibit intravascular coagulation, for instance: blood composition, factors that influence activation or inhibition of platelets, factors that influence activation or inhibition of a clotting cascade (e.g., at any point in a multilayered cascade), anti-coagulant presence or usage versus no anti-coagulation presence or usage, viscosity of blood (since dialysis patients may be anemic), etc. Factors that influence activation or inhibition of platelets may include, for example, initiation of platelet aggregation inhibition. The coagulation models may further account for shear rate and/or chemical pathways, for instance, in modeling the blood flow of a patient using anticoagulants.

In one embodiment, T may be calculated by advecting particles using the blood velocity field calculated from the hemodynamics. For example, particles may be defined based on a platelet activation function, which, in turn, may be defined based on a velocity gradient (e.g., with a deformation tensor). For instance, an active platelet may be identified when an activation threshold is crossed. Calculating T may then involve tracing the evolution or activity of the active platelet over time. Another exemplary platelet activation model may include a power law model based on shear stresses, in which advecting particles may involve releasing simulated blood cells at the inlet of a problem geometry and propagating the cells based on the blood velocity field to trace the path of the simulated blood cells over a period of time. Such a power law model may be used to calculate the residence time of the blood cells, which quantifies the propensity of the blood cells to form clots. For instance, the higher the residence time, the higher the propensity for thrombus formation. A patient's blood viscosity may affect the velocity field and, consequently, the residence time.

Any other term encoding hemodynamic quantities of interest that may be added to the cost function, which may be represented by the term $\Sigma_{i=1}^{N}\beta_i f_i(P,v)$. Non-linear combinations of the terms may also be used.

To find an optimal treatment, one embodiment of step 223 may include selecting or identifying an optimization method to find the parameters that minimize the cost function C. Any optimization method, including (i) derivative-free optimization techniques (e.g., pattern search, Nelder-Mead algorithm, etc.), (ii) gradient-based quasi-Newtonian algorithm (e.g., BFGS), or (iii) global optimization methods (e.g., evolutionary search algorithm) may be used to find the optima. Constraints may be incorporated by mapping parameters in the constraint region to a very high value (e.g., 10^10). Step 225 may include performing the optimization method, and step 227 may include outputting the results of the optimization method and/or updating or changing the cost function to solve for a different optima.

FIG. 3A is a block diagram of an exemplary method 300 of performing predictive modeling and simulation of an AVG between the brachial artery and antecubital vein, which is one exemplary embodiment of simulating hemodialysis access. FIG. 3B is a block diagram of an exemplary method 320 of optimizing an AVG, according to an exemplary embodiment. The methods of FIGS. 3A and 3B may be performed by server systems 106, based on information, images, and data received from physicians 102 and/or third party providers 104 over electronic network 101. Exemplary methods 300 and 320 may apply to an AVG between any other artery and vein as well. Furthermore, exemplary methods 300 and 320 may be extended to an AVF where graft-specific parameters, e.g., radius, may be removed from the optimization parameter set.

In one embodiment, step 301 may include acquiring a digital representation of a system (e.g., a patient's vasculature or anatomy of interest) and reconstructing a computational model to represent a hemodynamic characteristic of the system. For example, the system and computational model may include a portion of a patient's aorta, brachial artery, antecubital vein, and (if available) other arteries, e.g., cephalic, subclavian, and radial artery. A three dimensional model of the brachial artery and antecubital vein, part of the aorta, and other visible arteries and veins may be reconstructed using a combination of automated algorithms and manual editing.

Step 301 may further include receiving or measuring available graft radii. Candidate sites or parameters for anastomoses in the artery and veins may also be measured or received as input, and infeasible surgical geometries may be used as constraints.

In one embodiment, step 303 may include computing hemodynamics in the model pre-AVG implantation. Blood flow simulations in the reconstructed geometry (e.g., from step 301) may be performed by constructing a finite element mesh of the computational model. Blood pressure and velocities may be calculated at the vertices of the finite element mesh, e.g., by solving the Navier-Stokes equations. At the inlet to the model, the aortic inlet flow and blood pressure may be coupled to a reduced-order heart model driven by a ventricular elastance function. At the outlets, resistance boundary conditions which relate blood pressure to flow-rate may be prescribed. These values may be obtained for different arteries by determining the ratio of population-averaged nominal pressure to nominal flow-rate. For instance, pressure and flow-rate for the radial artery may be ~150 mm Hg and ~600 ml/min, respectively. Hemodynamic quantities of interest may be calculated from blood pressure and velocity found using the Navier-Stokes equations.

In one embodiment, step 305 may include modeling a virtual AVG. For example, step 305 may include constructing a virtual model of the AVG by inserting a graft at candidate sites (e.g., sites provided in step 301). This may be performed by creating a cylindrical vessel of the radius (e.g., from step 301) and creating an anastomosis using the cylindrical vessel and a series of Boolean operations on the computational geometry constructed from step 301. Alternatively, if an implicit representation of the patient-specific geometry is available, an implicit model of a cylindrical graft may be used to model the geometric changes associated with inserting a graft. In one embodiment, this procedure may be performed twice, once at the brachial artery and once at the antecubital vein. A finite element mesh of the new geometry may be constructed.

In one embodiment, step 307 may include calculating hemodynamic quantities of interest post-implantation of an AVG. In one embodiment, step 309 may include reporting a comparison of the pre-AVG hemodynamic quantities of interest to modeled post-AVG hemodynamic quantities of interest. For example, step 309 may include reporting the comparison for one or more of the candidate AVG parameters that were provided as input in step 301.

Regarding FIG. 3B, method 320 shown in FIG. 3B may include optimizing the radius and location of an AVG. In one embodiment, step 321 of method 320 may include defining a cost function for optimizing AVG implantation. The cost function may include parameters that contribute to AVG optimization. For example, one parameter may include graft radius. Graft radius may affect shunting resistance of the AVG. A higher graft radius may result in larger blood flow being shunted through the AVG. Length, as well as curvature of vascular graft, may also be treated as a parameter. The curvature of the graft may be important since the graft may go down the forearm, take a 180° turn, and return to the antecubital space. Further, the angle of the AVG may impact the local hemodynamics and may result in adverse hemodynamics, e.g., flow stasis, recirculation, etc. Location of anastomosis may be another parameter which impacts the outcome of treatment. The graft may take various different pathways, e.g., depending on the location of the arterial and venous anastomosis. A desired output of the model may include a choice of an optimal site for anastomosis. An exemplary cost function may be defined as $$C = \frac{(E_{post} - E_{pre})}{E_{pre}} - \frac{(Q_{dialyzer})}{Q_{max}} - \frac{(Q_{distal})}{Q_{max}} + \frac{(H_{post} - H_{pre})}{H_{pre}} + \frac{(T - T_{pre})}{T_{pre}}$$

The first, second, and last terms of the above equation may be the same as defined in the general embodiment (and normalized by their nominal value). An AVG-specific term (e.g., $Q_{distal}$) may be added to ensure that most of the flow is not shunted and that enough blood flow goes to the extremities. This may help prevent a condition where a patient loses sensation or has compromised circulation in extremities soon after the surgery. Specifically, $Q_{distal}$ may be the blood flow distal to the arterial anastomosis site.

In one embodiment, step 323 may include receiving, creating, or identifying a termination criterion. In one embodiment, step 325 may include using a derivative-free Nelder-Mead optimization method to compute parameters that may minimize the cost function. A random initial parameter set may be chosen. Subsequently, at each step in the Nelder-Mead algorithm, a new parameter may be identified by constructing simplexes using existing points and choosing an operation between reflection, reduction, contraction or reduction. In one embodiment, step 327 may include determining whether the computed parameters from step 325 meet a termination criterion and performing step 325 successively until the termination criterion is reached. In one embodiment, step 329 may include outputting the parameters computed where the termination criterion was met, as optimal therapy parameters, e.g., to an electronic storage medium and/or to a user interface.

Hemodialysis may present its own set of risks, including cardiovascular risks stemming from dialysis access. Various access treatments may change vessel geometry, altering hemodynamics and causing thrombosis or dangerous levels of cardiac demand. A desire exists to ensure that there is enough blood flow to allow successful dialysis while also ensuring that change to hemodynamics does not endanger a patient. The present disclosure thus provides systems and methods to improve treatment planning by predicting changes in hemodynamics that may result from vascular access procedures. The systems and methods include simulating access treatments and comparing results from the simulations to provide optimal treatments for a patient.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of selecting hemodialysis access treatment options that reduce propensity for thrombosis, the method comprising:
   receiving a pre-treatment patient-specific anatomic model comprising pre-treatment geometry of a patient's vasculature;
   receiving a plurality of vascular access treatment options;
   modifying the pre-treatment patient-specific anatomic model to generate, for each vascular access treatment option of the received plurality of vascular access treatment options, a respective patient-specific anatomic model of a post-treatment geometry, given the respective vascular access treatment option;
   generating, for each patient-specific anatomic model of a post-treatment geometry, a computational model of a hemodynamic characteristic of the respective patient-specific anatomic model;
   calculating, for each vascular access treatment option of the received plurality of vascular access treatment options, a value of the hemodynamic characteristic using the respective computational model, the hemodynamic characteristic including vessel shear stress and/or particle residence time through a vessel of the respective vascular access treatment option;
   calculating, for each vascular access treatment option of the received plurality of vascular access treatment options, a propensity for thrombosis associated with the respective vascular access treatment option and one or more characteristics of the patient's blood;
   generating and solving a cost function using the estimated value of the hemodynamic characteristic of each patient-specific anatomic model of a post-treatment geometry and the calculated propensity for thrombosis of each vascular access treatment option;
   selecting, using the solved cost function, a vascular access treatment option for the patient, in which the propensity for thrombosis associated with the selected vascular access treatment option is lower than a propensity for thrombosis associated with a non-selected vascular access treatment option; and
   outputting the selected vascular access treatment option to a user interface, the output including one of graphical, pictorial, and interactive features.

2. The computer-implemented method of claim 1, further comprising:
   reporting post-treatment blood pressure, blood velocity, perfusion pressure, blood flow, cardiac demand, or cardiac output of the patient based on the selected vascular access treatment option.

3. The computer-implemented method of claim 1, further comprising:
   receiving or determining a geometry of a vascular access treatment option of the plurality of vascular access treatment options; and
   modifying the received pre-treatment patient-specific anatomic model such that the post-treatment geometry is based on the received or determined geometry of a vascular access treatment option.

4. The computer-implemented method of claim 1, wherein the plurality of vascular access treatment options includes a graft.

5. The computer-implemented method of claim 1, further comprising:
   receiving or measuring one or more candidate locations for a vascular access treatment option of the plurality of vascular access treatment options;
   determining the respective patient-specific anatomic model at at least one of the one or more candidate locations.

6. The computer-implemented method of claim 1, wherein the cost function is generated and solved based on blood flow through vessels distal to a location of the respective vascular access treatment option.

7. The computer-implemented method of claim 1, further comprising:
   calculating the propensity for thrombosis by modeling particles advecting through a blood velocity field.

8. The computer-implemented method of claim 1, wherein the cost function is generated and solved based on patient medical history.

9. A system for selecting hemodialysis access treatment options that reduce propensity for thrombosis, the system comprising:
a data storage device storing instructions for simulating or optimizing hemodialysis access; and
a processor configured to execute the instructions to perform a method including:
receiving a pre-treatment patient-specific anatomic model comprising pre-treatment geometry of a patient's vasculature;
receiving a plurality of vascular access treatment options;
modifying the pre-treatment patient-specific anatomic model to generate, for each vascular access treatment option of the received plurality of vascular access treatment options, a respective patient-specific anatomic model of a post-treatment geometry, given the respective vascular access treatment option;
generating, for each patient-specific anatomic model of a post-treatment geometry, a computational model of a hemodynamic characteristic of the respective patient-specific anatomic model;
calculating, for each vascular access treatment option of the received plurality of vascular access treatment options, a value of the hemodynamic characteristic using the respective computational model, the hemodynamic characteristic including vessel shear stress and/or particle residence time through a vessel of the respective vascular access treatment option;
calculating, for each vascular access treatment option of the received plurality of vascular access treatment options, a propensity for thrombosis associated with the respective vascular access treatment option and one or more characteristics of the patient's blood;
generating and solving a cost function using the estimated value of the hemodynamic characteristic of each patient-specific anatomic model of a post-treatment geometry and the calculated propensity for thrombosis of each vascular access treatment option;
selecting, using the solved cost function, a vascular access treatment option for the patient, in which the propensity for thrombosis associated with the selected vascular access treatment option is lower than a propensity for thrombosis associated with a non-selected vascular access treatment option; and
outputting the selected vascular access treatment option to a user interface, the output including one of graphical, pictorial, and interactive features.

10. The system of claim 9, wherein the system is further configured for:
reporting post-treatment blood pressure, blood velocity, perfusion pressure, blood flow, cardiac demand, or cardiac output of the patient based on the selected vascular access treatment option.

11. The system of claim 9, wherein the system is further configured for:
receiving or determining a geometry of a vascular access treatment option of the plurality of vascular access treatment options; and
modifying the received pre-treatment patient-specific anatomic model such that the post-treatment geometry is based on the received or determined geometry of a vascular access treatment option.

12. The system of claim 9, wherein the plurality of vascular access treatment options includes a graft.

13. The system of claim 9, wherein the system is further configured for:
receiving or measuring one or more candidate locations for a vascular access treatment option of the plurality of vascular access treatment options;
determining the respective patient-specific anatomic model at at least one of the one or more candidate locations.

14. The system of claim 9, wherein the cost function is generated and solved based on blood flow through vessels distal to a location of the respective vascular access treatment option.

15. The system of claim 9, wherein the system is further configured for:
calculating the propensity for thrombosis by modeling particles advecting through a blood velocity field.

16. The system of claim 9, wherein the cost function is generated and solved based on patient medical history.

17. A non-transitory computer readable medium for use on a computer system containing computer-executable programming instructions for performing a method of selecting hemodialysis access treatment options that reduce propensity for thrombosis, the method comprising:
receiving a pre-treatment patient-specific anatomic model comprising pre-treatment geometry of a patient's vasculature;
receiving a plurality of vascular access treatment options;
modifying the pre-treatment patient-specific anatomic model to generate, for each vascular access treatment option of the received plurality of vascular access treatment options, a respective patient-specific anatomic model of a post-treatment geometry, given the respective vascular access treatment option;
generating, for each patient-specific anatomic model of a post-treatment geometry, a computational model of a hemodynamic characteristic of the respective patient-specific anatomic model;
calculating, for each vascular access treatment option of the received plurality of vascular access treatment options, a value of the hemodynamic characteristic using the respective computational model, the hemodynamic characteristic including vessel shear stress and/or particle residence time through a vessel of the respective vascular access treatment option;
calculating, for each vascular access treatment option of the received plurality of vascular access treatment options, a propensity for thrombosis associated with the respective vascular access treatment option and one or more characteristic of the patient's blood;
generating and solving a cost function using the estimated value of the hemodynamic characteristic of each patient-specific anatomic model of a post-treatment geometry and the calculated propensity for thrombosis of each vascular access treatment option;
selecting, using the solved cost function, a vascular access treatment option for the patient, in which the propensity for thrombosis associated with the selected vascular access treatment option is lower than a propensity for thrombosis associated with a non-selected vascular access treatment option; and
outputting the selected vascular access treatment option to a user interface, the output including one of graphical, pictorial, and interactive features.

18. The non-transitory computer readable medium of claim 17, the method further comprising:

reporting post-treatment blood pressure, blood velocity, perfusion pressure, blood flow, cardiac demand, or cardiac output of the patient based on the selected vascular access treatment option.

19. The non-transitory computer readable medium of claim 17, the method further comprising:
receiving or determining a geometry of a vascular access treatment option of the plurality of vascular access treatment options; and
modifying the received pre-treatment patient-specific anatomic model such that the post-treatment geometry is based on the received or determined geometry of a vascular access treatment option.

20. The non-transitory computer readable medium of claim 17, wherein the plurality of vascular access treatment options includes a graft.

* * * * *